(12) United States Patent
Smith et al.

(10) Patent No.: US 9,393,118 B2
(45) Date of Patent: Jul. 19, 2016

(54) IMPLANTS WITH ROUGHENED SURFACES (71) Applicant: DEPUY SYNTHES PRODUCTS, INC., Raynham, MA (US)

(72) Inventors: Bryan J. Smith, Fort Wayne, IN (US); Jeffrey A. Rybolt, Fort Wayne, IN (US); Hengda D. Liu, Warsaw, IN (US); Andrew J. Martin, Carmel, NY (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/488,854

(22) Filed: Sep. 17, 2014

(65) Prior Publication Data
US 2015/0157460 A1    Jun. 11, 2015

Related U.S. Application Data (62) Division of application No. 12/470,397, filed on May 21, 2009, now Pat. No. 8,871,142.

(60) Provisional application No. 61/055,304, filed on May 22, 2008.

(51) Int. Cl.
*B22F 1/00* (2006.01)
*A61F 2/28* (2006.01)
(Continued)

(52) U.S. Cl.
CPC . *A61F 2/28* (2013.01); *A61L 27/04* (2013.01); *A61L 27/50* (2013.01); *B22F 3/1121* (2013.01);
(Continued)

(58) Field of Classification Search
CPC .................................... B22F 3/1121

USPC ........................................... 419/26
See application file for complete search history.

(56) References Cited

U.S. PATENT DOCUMENTS 3,852,045 A    12/1974 Wheeler et al.
3,855,638 A    12/1974 Pilliar
(Continued)

FOREIGN PATENT DOCUMENTS

DE    102006005034 A1    8/2007
EP    1779812 A1    5/2007
(Continued)

OTHER PUBLICATIONS

Wen, CE et al., Novel titanium foam for bone tissue engineering, Journal of Materials Research, vol. 17, No. 10, pp. 2633-2639, 2002.*
(Continued)

*Primary Examiner* — Jessee Roe
*Assistant Examiner* — Christopher Kessler (57) ABSTRACT

Provided are methods for processing a green body that includes compacted metal powder, comprising impacting the green body with a particulate material for a time and under conditions effective to displace a portion of the metal powder from the green body. The present methods can be used to prepare green bodies that have "roughened" surfaces and that can be used to make orthopedic implants displaying low movement relative to bone when installed in situ, which corresponds to higher stability upon implantation and decreases the time required for biological fixation of the implant. Also provided are implants comprising a metallic matrix, and methods comprising surgically installing an implant prepared from a "surface roughened" green body in accordance with the present invention.

14 Claims, 6 Drawing Sheets

(51) Int. Cl.
*A61L 27/04* (2006.01)
*A61L 27/50* (2006.01)
*B22F 3/11* (2006.01)
*C22C 14/00* (2006.01)
*A61F 2/30* (2006.01)

(52) U.S. Cl.
CPC .............. *B22F 3/1146* (2013.01); *C22C 14/00* (2013.01); *A61F 2/3094* (2013.01); *A61F 2002/30968* (2013.01); *A61F 2310/00017* (2013.01); *A61F 2310/00023* (2013.01); *A61F 2310/00029* (2013.01); *A61F 2310/00089* (2013.01); *A61F 2310/00095* (2013.01); *A61F 2310/00101* (2013.01); *A61F 2310/00131* (2013.01); *A61L 2400/18* (2013.01); *B22F 2998/10* (2013.01)

(56) References Cited

U.S. PATENT DOCUMENTS

| | | | |
|---|---|---|---|
| 4,156,943 | A | 6/1979 | Collier |
| 4,206,516 | A | 6/1980 | Pilliar |
| 4,479,271 | A | 10/1984 | Bolesky et al. |
| 4,612,160 | A | 9/1986 | Donlevy |
| 4,944,760 | A | 7/1990 | Kenna |
| 4,954,170 | A | 9/1990 | Fey et al. |
| 5,104,410 | A | 4/1992 | Chowdhary |
| 5,201,766 | A | 4/1993 | Georgette |
| 5,251,468 | A | 10/1993 | Lin et al. |
| 5,308,556 | A | 5/1994 | Bagley |
| 5,344,494 | A | 9/1994 | Davidson et al. |
| 5,368,881 | A | 11/1994 | Kelman |
| 5,605,491 | A | 2/1997 | Yam et al. |
| 5,658,333 | A | 8/1997 | Kelman |
| 5,732,469 | A | 3/1998 | Hamamoto |
| 5,765,095 | A | 6/1998 | Flak et al. |
| 5,766,257 | A | 6/1998 | Goodman |
| 5,826,586 | A | 10/1998 | Mishra et al. |
| 5,984,969 | A | 11/1999 | Matthews et al. |
| 5,989,027 | A | 11/1999 | Wagner et al. |
| 6,042,780 | A | 3/2000 | Huang |
| 6,123,896 | A | 9/2000 | Meeks et al. |
| 6,135,857 | A | 10/2000 | Shaw et al. |
| 6,524,522 | B2 | 2/2003 | Vaidyanathan et al. |
| 6,582,470 | B1 | 6/2003 | Lee et al. |
| 6,592,787 | B2 | 7/2003 | Pickrell et al. |
| 6,660,224 | B2 | 12/2003 | Lefebvre et al. |
| 6,846,327 | B2 | 1/2005 | Khandkar et al. |
| 6,849,230 | B1 | 2/2005 | Feichtinger |
| 6,852,272 | B2 | 2/2005 | Artz et al. |
| 7,018,418 | B2 | 3/2006 | Amrich et al. |
| 7,018,583 | B2 | 3/2006 | Berger et al. |
| 7,147,819 | B2 | 12/2006 | Bram et al. |
| 7,175,665 | B2 | 2/2007 | German et al. |
| 2003/0035747 | A1 | 2/2003 | Anderson et al. |
| 2003/0044301 | A1 | 3/2003 | Lefebvre et al. |
| 2003/0075013 | A1 | 4/2003 | Grohowski |
| 2003/0153981 | A1 | 8/2003 | Wang et al. |
| 2004/0049284 | A1 | 3/2004 | German et al. |
| 2004/0102854 | A1 | 5/2004 | Zhu |
| 2004/0167633 | A1 | 8/2004 | Wen et al. |
| 2005/0100578 | A1 | 5/2005 | Schmid et al. |
| 2005/0249625 | A1 | 11/2005 | Bram et al. |
| 2006/0002810 | A1 | 1/2006 | Grohowski, Jr. |
| 2006/0163774 | A1 | 7/2006 | Abels et al. |
| 2006/0178749 | A1 | 8/2006 | Pendleton et al. |
| 2006/0228247 | A1 | 10/2006 | Grohowski |
| 2006/0241781 | A1 | 10/2006 | Brown |
| 2006/0246397 | A1 | 11/2006 | Wolf |
| 2007/0172380 | A1 | 7/2007 | Tatsumoto et al. |
| 2007/0173948 | A1 | 7/2007 | Meridew et al. |
| 2007/0196230 | A1 | 8/2007 | Hamman et al. |
| 2008/0009622 | A1 | 1/2008 | Takahashi et al. |
| 2008/0147187 | A1 | 6/2008 | Bollinger et al. |
| 2008/0199720 | A1 | 8/2008 | Liu |
| 2008/1099720 | | 8/2008 | Liu |
| 2008/0215098 | A1 | 9/2008 | Imwinkelried et al. |
| 2009/0084491 | A1 | 4/2009 | Uthgenannt et al. |
| 2009/0292365 | A1 | 11/2009 | Smith et al. |
| 2011/0009974 | A1 | 1/2011 | Blaylock et al. |
| 2011/0029092 | A1 | 2/2011 | Deruntz et al. |

FOREIGN PATENT DOCUMENTS

| | | |
|---|---|---|
| JP | 62205201 A | 9/1987 |
| JP | 2007-075485 | 3/2007 |
| WO | WO 2005/009489 A2 | 2/2005 |
| WO | WO 2005/009729 A2 | 2/2005 |
| WO | WO 2006/014294 A1 | 2/2006 |
| WO | WO 2006/079459 | 8/2006 |
| WO | WO 2006/130350 A2 | 12/2006 |
| WO | WO 2006/130350 A3 | 12/2006 |
| WO | WO 2009/143420 | 11/2009 |

OTHER PUBLICATIONS

Bozkaya, D. et al.: "Mechanics of the taper integrated screwed-in (TIS) abutments used in dental implants" J. of Biomechanics, vol. 38, No. 1, Jan. 1, 2005, pp. 87-97, XP027738016.

German, Randall: "Powder Injection Molding," ASM Handbook, vol. 7 (1998), pp. 355-364.

Grant, J.A. et al.: "Artificial composite bone as a model of human trabecular bone: The implant-bone interface", J. of Biomechanics vol. 40, No. 5, Jan. 1, 2007, pp. 1158-1164 (XP055073219).

International Standard ISO 4287:1997; Geometrical Product Specifications (GPS)—Surface Texture: Profile Method—Terms, Definitions and Surface Texture Parameters, Technical Corrigendum 2, 2005, 2 pages.

International Standard ISO 4287:1997; Geometrical Product Specifications (GPS)—Surface Texture: Profile Method—Terms, Definitions and Surface Texture Parameters, Technical Corrigendum 1, 1998, 2 pages.

International Standard ISO 4287:1997; Geometrical Product Specifications (GPS)—Surface Texture: Profile Method—Terms, Definitions and Surface Texture Parameters, 1997, 32 pages.

Phelly Materials, Inc. "Hydride and Dehydride CP Ti and Ti-6A1-4V Powders", 2007, 1 page.

Phelly Materials, Inc. "Pure Metal Powder", 2007, 1 page.

Wen, C.E. et al., Novel Titanium foam for Bone Tissue Engineering, Journal of Materials Research, vol. 17, No. 10, pp. 2633-2639.

Zeiss, C., Zeiss Surfcomm 5000—"Contour and Surface Measuring Machines", 2005, 16 pages.

\* cited by examiner

FIG. 1

FIG. 2A unprocessed — unprocessed

FIG. 2B unprocessed — unprocessed

Blasted 75% Porous Ti-6Al-4V Foam Roughness - Pa

FIG. 9

Blasted 75% Ti-6Al-4V Foam Roughness - Pp

*FIG. 10* a
IMPLANTS WITH ROUGHENED SURFACES

CROSS REFERENCE TO RELATED APPLICATIONS

This divisional application claims the benefit of U.S. application Ser. No. 12/470,397, filed May 21, 2009, now U.S. Pat. No. 8,871,142, which claims priority to U.S. Provisional Application No. 61/055,304, filed May 22, 2008.

FIELD OF THE INVENTION

The present invention relates to orthopedic implants and materials used for making orthopedic implants, as well as methods for producing and using such implants and materials.

BACKGROUND OF THE INVENTION

The "space holder" method is a well-known process for making metallic foam structures and employs dissolvable or otherwise removable space-holding materials that are combined with metallic powders and subsequently removed from the combination by various methods, including heat or liquid dissolution, leaving behind a porous matrix formed from the metallic powder. The porous matrix material is then sintered to further strengthen the matrix structure. Numerous variations on the space holder concept are known in the art. See, e.g., U.S. Pat. Nos. 3,852,045; 6,849,230; U.S. Pub. Nos. 2005/0249625; 2006/0002810.

Surface roughness is an important attribute of orthopedic implants that are intended for cementless fixation to bone. High surface roughness can correspond to elevated friction against bone and general stability upon initial implantation, both of which are conducive to long-term stability via bone and tissue ingrowth. Several porous coating products have been developed for use in connection with implant surfaces, including implant coatings that are said to enhance biological fixation and maximize tissue ingrowth. Such coatings are applied to the face of an implant in order to impart a rough, high friction surface that interacts with bone in a manner that leads to a decrease in relative movement between the implant and the bone while providing a network of interconnected pores for secure fixation of the implant to bone by the ingrowth of bone tissue.

SUMMARY OF THE INVENTION

In one aspect, the present invention provides methods for processing a green body that includes compacted metal powder comprising impacting the green body with a particulate material under conditions effective to displace a portion of the metal powder from the green body.

Also provided are implants comprising a metallic matrix, wherein at least one surface of the metallic matrix has a static friction coefficient with a polymer bone analog of about 0.7 or higher. Also disclosed are implants comprising a metallic matrix, wherein at least one surface of the metallic matrix has a roughness that corresponds to a Pa value of at least about 20, a roughness that corresponds to a Pp value of at least about 60, a roughness that corresponds to a Pt value of at least about 140, or a roughness that corresponds to a Pq value of at least about 30.

The present methods also include surgically installing an implant made in accordance with the disclosed processing techniques.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "a material" is a reference to one or more of such materials and equivalents thereof known to those skilled in the art, and so forth. When values are expressed as approximations, by use of the antecedent "about," it will be understood that the particular value forms another embodiment. As used herein, "about X" (where X is a numerical value) refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable.

The disclosures of each patent, patent application, and publication cited or described in this document are hereby incorporated herein by reference, in their entirety.

Porous coating products may be applied to one or more of the outer surfaces of shaped implants to increase friction between such implants and bone while providing a network of interconnected pores for secure fixation of the implant to bone by the ingrowth of bone tissue. Rough surface coatings exhibit peaks that, when present on an implant face, are believed to lead to increased contact pressure and thereby ploughing and abrasive interaction between the implant face and the surface of an adjoining bone. Such phenomena at the surface of the implant increase the resistance to relative movement between the implant and bone, which corresponds to higher stability upon implantation and may increase the likelihood of achieving biological fixation of the implant.

The present invention represents a companion method or an alternative to the use of porous coating products on the surface of orthopedic implants comprising a metallic matrix. It has presently been discovered that the surface topography of a green body, i.e., an article comprising a compacted but unsintered mass comprising metal powder, may be altered by displacing portions of the compacted metal powder from the surface of the green body. The resulting topography is characterized at least in part by pits or valleys and peaks, which, much like a coated surface of an implant, allows an implant formed from such green body to exhibit increased friction with an abutting bone surface. The attendant benefits of such increased friction are evident in view of the preceding discussion, and include implant stability and increased likelihood of biological fixation through successful integration with bone and tissue. Unlike a coated implant, however, the topography of the resulting implant is an inherent characteristic of the implant itself and does not derive from the use of a substance other than the implant material. Thus, the presently disclosed approach has the potential to reduce the cost of preparing orthopedic implants, at least because a surface coating need not be separately acquired.

In accordance with the present invention there are provided methods for processing a green body that includes compacted metal powder, such methods comprising impacting the green body with a particulate material for a time and under conditions effective to displace a portion of the metal powder from the green body. Also provided are green bodies that include compacted metal powder, the green body having been impacted with a particulate material for a time and under conditions effective to displace a portion of the metal powder from the green body. The present methods may further include sintering the green body following the displacement of a portion of the metal powder from the green body. A sintered green body, which may optionally undergo machining or other processing steps following such sintering, can function as an orthopedic implant that may be installed within a patient. Accordingly, the present methods may further comprise surgically installing into a patient an implant made from a green body that has been processed and sintered in accordance with the present invention.

The green body that is impacted with the particulate material may be prepared using traditional techniques. The preparation of a green body may comprise mixing at least one metal powder with an extractable material, thereby forming a powder mixture in which the metal powder and the extractable material assume respective positions, shaping the powder mixture into a shaped object, and compacting the shaped object to form the green body.

The metal powder may comprise any biocompatible metal, nonlimiting examples of which include titanium, a titanium alloy, a cobalt-chromium alloy, molybdenum, tantalum, niobium, zirconium, stainless steel, or any combination thereof. The extractable material may be a material that is soluble in an aqueous fluid, an organic solvent, or both, and may include a salt, a sugar, a solid hydrocarbon, a urea derivative, a polymer, or any combination thereof. Suitable examples include sodium chloride, potassium chloride, sucrose, potassium sorbate, carbamide, biuret, ammonium carbonate, ammonium bicarbonate, naphthalene, or any combination thereof. Alternatively, the extractable material may be removed under heat and/or pressure conditions; for example, the extractable material may volatilize, melt, or otherwise dissipate as a result of heating. Examples of such extractable materials include ammonium bicarbonate, urea, biuret, melamine, ammonium carbonate, naphthalene, sodium bicarbonate, and any combination thereof.

Suitable techniques for mixing a metal powder with an extractable material will be readily appreciated by those skilled in the art. See, e.g., U.S. Pat. Nos. 3,852,045, 6,849,230; U.S. Pub. Nos. 2005/0249625, 2006/0002810. Ideally, the mixing results in a substantially uniform dispersion of the particles comprising the minor component of the powder mixture among the particles comprising the major part of the powder mixture. The metal powder may comprise about 18 to about 67 weight percent of the powder mixture, the balance of the powder mixture comprising the extractable material. Once the extractable material is removed from the green body in later stages of the present methods, the resulting porosity of the green body may be about 50% to about 90%, preferably about 60% to about 85%. The removal of the extractable material is described more fully infra.

Following the mixing of the at least one metal powder with the extractable material, the powder mixture may be shaped into a shaped object. The shaping process can comprise filling a mold with the powder mixture, the mold having at least roughly the three-dimensional parameters of the desired final implant product, allowing for subsequent processing steps such as machining. In other embodiments, the mold need not be designed to produce near-net shape parts or parts whose molded form resembles the desired final, sintered part; molds may produce generic shapes, such as bars, rods, plates, or blocks, that may be subsequently machined in the green state to produce a part that after sintering-induced shrinkage closely approximates the desired shape of the final product, with optional machining of the sintered part. Molds and mold assemblies for such purposes are well known among those skilled the art and may allow for the preparation of bodies that are, for example, spherical, spheroid, ovoid, hemispherical, cuboid, cylindrical, toriod, conical, concave hemispherical (i.e., cup-shaped), irregular, or that adopt any other desired three-dimensional conformation. Once formed from the powder mixture in accordance with the preceding, the resulting shaped object may be compacted to form the green body. The shaped object is compacted while contained within a mold assembly. Compacting may be uniaxial, multi-axial, or isostatic. In preferred embodiments, a cold isostatic press is used to compact the shaped object into the green body. Following the compacting procedure, the resulting green body may be removed from the mold and processed. Processing may include machining or otherwise refining the shape of the green body.

Whether or not machining is performed after compacting, the green body may then be exposed to a solvent in which the extractable material is soluble. As indicated above, the extractable material may be soluble in an aqueous solvent, an organic solvent, or both. The exposure of the green body to the solvent may comprise immersing the green body in the solvent, for example, by immersing the green body in a bath comprising the solvent for a time sufficient to remove at least some of the extractable material. Depending on various factors such as the type of solvent chosen relative to the identity of the extractable material, the temperature of the solvent, and the time of exposure to the solvent, the removal of extractable material from the green body can range from partial to complete. The exposure of the green body to the solvent in which the extractable material is soluble preferably removes the extractable material from at least the surface of the green body to a depth at least about 1 mm, at least about 3 mm, at least about 5 mm, at least about 7 mm, or at least about 10 mm from any given surface of the green body.

In another embodiment, the extractable material is insoluble in aqueous or organic solvent, and is removable under heating conditions. In such circumstances, after the formation of the green body via compacting (and whether or not machining is performed following compacting) the green body may be heated for a time and under conditions effective to evaporate at least some of the extractable material yet substantially maintain the metal powder in its position in the green body. Depending on various factors such as the identity of the extractable material, the temperature of the heating environment, and the time of heating, the removal of extractable material from the green body can range from partial to complete, and the heating of the green body preferably removes the extractable material from at least the surface of the green body, down to at least about 5% of the total depth of the green body. Preferably, the thermal removal of extractable material is performed at temperatures much lower than sintering temperature, in order to avoid contamination of the green body material with C, N, or H from organic space holders. For example, the thermal removal of extractable material may occur at less than about 100° C., which is sufficient to cause the decomposition of some extractable materials, such as ammonium bicarbonate.

A green body in accordance with the present invention may be impacted with a particulate material for a time and under conditions effective to displace a portion of the metal powder from the green body. The displacement of a portion of the metal powder from the green body alters the surface geometry of the green body. The altered surface geometry may be described as "roughness" and is generally characterized, at least in part, by regular or irregular pits (or valleys) and peaks. In accordance with the present invention, roughness can be varied by numerous factors including the force with which the particulate material impacts the green body, the characteristics of the particulate material (including material type, and particle size and shape), the distance between the source of the particulate material and the green body, the geometry of the orifice from which the particulate material is ejected (when impacting is performed by ejecting the particulate material from an orifice), and the characteristics of the green body itself, including the porosity of the surface region of the green body (which derives from the ratio of metal powder to extractable material during the fabrication of the green body) and the pressure at which the metal powder and space holder particle mixture is compacted to form the green body.

The particulate material that is used for impacting the green body may be soluble in an aqueous solvent, an organic solvent, or both. The particulate material may include a salt, a sugar, a solid hydrocarbon, a urea derivative, a polymer, or any combination thereof. Suitable examples include sodium chloride, potassium chloride, sucrose, potassium sorbate, carbamide, biuret, ammonium carbonate, ammonium bicarbonate, naphthalene, or any combination thereof. Additionally or alternatively, the particulate material may be removable under heat and/or pressure conditions; for example, the particulate material may volatilize, melt, or otherwise dissipate as a result of heating. Examples of such particulate materials include ammonium bicarbonate, urea, biuret, melamine, ammonium carbonate, naphthalene, sodium bicarbonate, and any combination thereof. The thermal removal of particulate material may be conducted as a heating cycle that is independent from any sintering step, or may be part of a continuous furnace cycle that at immediately precedes and "ramps up" to sintering. Preferably, the thermal removal of particulate material is performed at temperatures much lower than sintering temperature, in order to avoid contamination of the green body material with C, N, or H from organic space holders. For example, the thermal removal of particulate material may occur at less than about 100.degree. C., which is sufficient to cause the decomposition of some particulate materials, such as ammonium bicarbonate.

The particulate material may comprise particles that are of irregular or varied shapes and a mixture of sizes, or may comprise particles that are of substantially uniform sizes, shapes, or both. For example, the particles of the particulate material may be substantially spherical, oblong, or may be crystalline and adopt any of a number of different crystal conformations. In one embodiment, the particulate material comprises particles having an average diameter (e.g., along the major dimension of any given particle) of about 150 µm to about 1250 µm.

The force with which the particulate material strikes the green body can affect the displacement of metal powder from the green body. The "force" with which the particulate material strikes the green body may be expressed in terms of pressure, for example, in units of pound-force-per-square-inch. In accordance with the present invention, the particulate material may impact the green body at a pressure of about 3 psi to about 30 psi, for example at about 5 psi, about 7 psi, about 10 psi, about 15 psi, about 20 psi, about 25 psi, about 27 psi, or about 30 psi. The amount of force/pressure with which the green body is impacted with the particulate material may vary during the process of impacting; for example, the force/pressure with which the green body is impacted may be increased over the course of the impacting process, may be decreased, or may be alternately decreased and increased.

In addition, the amount of time during which the impacting is effected can affect the displacement of the metal powder from the green body. In certain embodiments, the impacting is effected for no more than about 2 seconds to about 2 minutes, preferably no more than about 2 seconds to about 30 seconds. The impacting time may depend upon part size; the "stream" of particulate material may be wide enough to cover the entire facing surface of certain small parts, whereas more time may be required if the part features more surface area. The impacting of the green body with the particulate material may be performed as a single episode, i.e., over a single, continuous period of time, or may occur as several episodes, for example, with one episode of impacting, followed by a period during which no impacting occurs, followed by a second episode of impacting, with this cycle optionally repeated one or more times. Each episode of impacting optionally is effected for no more than about 1 second to about 2 minutes, preferably no more than about 1 second to about 30 seconds.

The impacting of the green body with the particulate material may be accomplished by ejecting the particulate material from a suitable structure, such as an orifice that is connected to a source of particulate material. The particulate material may be ejected from an orifice that is positioned about 2 inches from about 30 inches from the green body during the impacting process. The orifice and the green body may be stationary with respect to one another, i.e., may be fixed such that the distance between them does not change during impacting. Alternatively, the impacting process may be carried out such that the distance between the green body and the orifice increases, decreases, or both during the impacting process.

The green body may be stationary during the impacting process, or may be rotated, laterally shifted, or otherwise spatially translated in order, for example, to allow multiple surfaces of the green body to be impacted by the particulate material. The same result may be achieved by changing the orientation of the source of the particulate material relative to the green body. In one example, the green body may be rotated at a given speed, or the speed with which the green body is rotated may vary over the course of the impacting process. The green body may be rotated at speeds varying from about 5 rpm to about 100 rpm, preferably from about 10 rpm to about 60 rpm, during impacting. In other embodiments the source of the particulate material may be moved relative to a stationary green body, for example, at a rate of about 0.1 in/s, about 0.2 in/s, about 0.25 in/s, about 0.5 in/s, about 1.0 in/s, about 1.5 in/s, about 2.0 in/s, about 2.5 in/s, about 3.0 in/s, about 3.5 in/s, about 4.0 in/s, or greater.

During the impacting process, there is a tendency for the particulate material to lodge into the surface of the green body. When the green body has been prepared using the "space holder" method, i.e., compacting a mixture of metal powder and extractable material, followed optionally by processing (such as machining), and by removal of at least a portion of the extractable material (either by treatment with solvent or by heating), it is also possible that some extractable material may remain within the green body. Accordingly, following the impacting process, the present methods may further comprise exposing the green body to a solvent in which the particulate material is soluble, in which the extractable material is soluble, or both. For example, if the particulate material is soluble in an aqueous fluid, the green body may be immersed in a bath comprising an aqueous fluid following the impacting process. The exposure of the green body to an aqueous fluid will remove all or substantially all of the particulate material from the impacting process, and may also serve to remove all or substantially all of any remaining extractable material. Alternatively, if the particulate material is not soluble in an aqueous or organic fluid but is instead removable by heat, any particulate material that is embedded in the green body can be removed via heating. Such heating may be accomplished during the "ramp up" period pursuant to a sintering process, which is traditionally performed with respect to a green body in order to prepare an implant.

Following the impacting process and, where necessary, the removal of particulate material and/or extractable material from the green body, the present methods may further comprise sintering the green body. Sintering is typically performed in a vacuum furnace and those skilled in the art will readily appreciate the appropriate conditions for sintering a green body comprising a metal powder. Sintering may be followed by additional processing steps, including machining to refine the shape characteristics of the sintered body.

Figure 1:
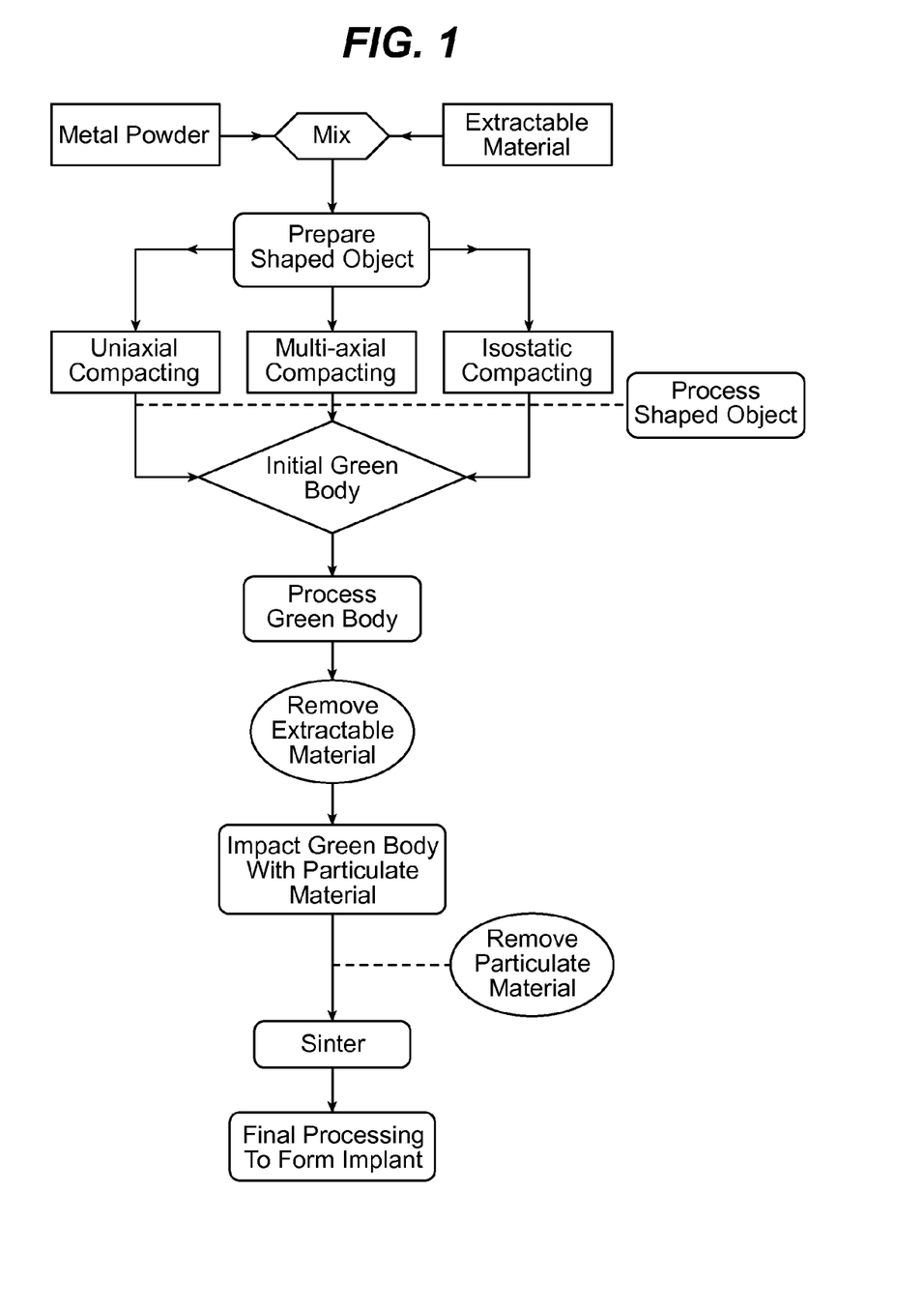
FIG. 1 is a schematic flowchart that illustrates methods in accordance with one aspect of the present invention.

An exemplary manufacturing process in accordance with the present invention is illustrated in FIG. 1. As described above, the process may begin by mixing at least one metal powder with an extractable material, shaping the powder mixture into a shaped object, compacting the shaped object to form a green body, and optional processing of the shaped object (e.g., by machining), followed by processing the green body, removal of the extractable material (such as by exposing the green body to a solvent in which the extractable material is soluble), impacting the green body with a particulate material, optionally removing the particulate material from the green body (for example, by exposing the green body to a solvent in which the particulate material is soluble), sintering the green body, and, if desired, final processing (e.g., by machining) in order to form an implant. In view of the preceding discussion, it will be apparent that various of the illustrated processing steps can be modified or altered, or in some cases entirely omitted, according to the needs of the manufacturer and/or the desired product. The schematic illustrated in FIG. 1 is but one embodiment and is intended to depict but one possible processing route in accordance with the present invention.

The present methods may further comprise surgically installing an implant made in accordance with the above-described impacting and sintering steps. An implant that is made in accordance with the recited impacting and sintering steps will possess characteristics that, as described above, are particularly well suited for ensuring stability upon surgical implantation, favorable biological fixation, and integration in situ with bone and tissue via ingrowth.

In accordance with the present invention there are also provided implants comprising a metallic matrix. One or more surfaces of the present implants may possess specific characteristics (e.g., static friction coefficient, various aspects of surface geometry), that are distinguishable from those that are present with respect to the surfaces of traditional implants. In one embodiment, at least one surface of the metallic matrix has a static friction coefficient of about 0.7 or higher with a polymer bone analog comprising polyurethane foam having a density of about 20 lb/ft$^3$. Implants comprising a metallic matrix that are coated on a surface with a porous coating product may yield a static friction coefficient of about 0.7 or higher with a polymer bone analog, but the static friction coefficient is attributable to the coating, not to the surface of the metallic matrix itself. In addition, the roughness of conventional porous coated products usually derives from the shape of the metal powders, wires, or fibers used to form the coating and their arrangement on the surface of the part, which is highly dependent upon how the coating is deposited on the substrate. In other embodiments of the present invention, at least one surface of the metallic matrix has a static friction coefficient of about 0.7 to about 1.5 with a polymer bone analog. Thus, the present implants provide a high static friction coefficient at one or more surfaces of the metallic matrix, unlike an implant that is coated at one or more surfaces with a porous coating product. The polymer bone analog comprising polyurethane provides a reference point with respect to the inventive implants. To the extent that the characteristics of the instant implants can be described by reference to a different friction substrate, the scope of instant invention should not be construed as being limited to implants that can only be described by reference to a polymer bone analog comprising polyurethane foam having a density of about 20 lb/ft$^3$. One example of the recited bone analog is Cat. No. FR-4520 from General Plastics Manufacturing Co. (Tacoma, Wash.), which is said to be a "rigid, closed-cell polyurethane foam" with a density of 20 lb/ft$^3$.

Also disclosed are implants or other articles of manufacture at least a portion of which comprises metallic matrix, wherein at least a second portion of which comprises a substrate material, which may be a solid substrate. For example, the implant or article of manufacture may comprise a layer or coating of metallic matrix material having a thickness of about 0.5 mm to about 50 mm, on at least a portion of a solid substrate. In such embodiments, one or more surfaces of the metallic matrix may possess specific characteristics (e.g., static friction coefficient, various aspects of surface geometry/roughness), that are distinguishable from those that are present with respect to the surfaces of traditional implants. Throughout the present disclosure, an "implant comprising a metallic matrix" may refer to an implant or article of manufacture that comprises a coating of metallic matrix material on at least a portion of a solid substrate.

The metallic matrix of the present implants and coatings may comprise titanium, a titanium alloy, a cobalt-chromium alloy, molybdenum, tantalum, niobium, zirconium, stainless steel, or any combination thereof.

Also provided are implants comprising a metallic matrix, wherein at least one surface of the metallic matrix has a roughness that corresponds to a Pa value of at least about 20, a roughness that corresponds to a Pp value of at least about 60, a roughness that corresponds to a Pt value of at least about 140, or a roughness that corresponds to a Pq value of at least about 30. The Pa parameter represents the arithmetic average value of the unfiltered raw profile departure from the mean line within a sampling length; Pp is the largest peak deviation of the unfiltered raw roughness profile from the mean line within a sampling length; Pt is the maximum peak to valley height of the unfiltered raw profile in the evaluation length; and Pq is the square root of the mean of all the 'z' values after they have been squared, defined over one sampling length. These parameters are pursuant to ISO 4287 (1997). In other embodiments the disclosed implants comprise a metallic matrix, wherein at least one surface of the metallic matrix has a roughness that corresponds to a Pa value of at least about 50, a roughness that corresponds to a Pp value of at least about 90, a roughness that corresponds to a Pt value of at least about 200, or a roughness that corresponds to a Pq value of at least about 60. In yet other embodiments of the present implants, at least one surface of the metallic matrix has a roughness that corresponds to a Pa value of at least about 70, a roughness that corresponds to a Pp value of at least about 120, a roughness that corresponds to a Pt value of at least about 300, or a roughness that corresponds to a Pq value of at least about 70.

Also provided are methods comprising surgically installing an implant comprising a metallic matrix, wherein at least one surface of the metallic matrix has a static friction coefficient of about 0.7 or higher with a polymer bone analog comprising polyurethane foam having a density of about 20 lb/ft$^3$. In another aspect, provided are methods comprising surgically installing an implant comprising a metallic matrix, wherein at least one surface of the metallic matrix has a static friction coefficient of about 0.7 to about 1.5 with a polymer bone analog. In other embodiments there are provided methods comprising surgically installing an implant comprising a metallic matrix, wherein at least one surface of the metallic matrix has a roughness that corresponds to a Pa value of at least about 20, a roughness that corresponds to a Pp value of at least about 60, a roughness that corresponds to a Pt value of at least about 140, or a roughness that corresponds to a Pq value of at least about 30. The implant comprising a metallic matrix may have at least one surface that has a roughness that corresponds to a Pa value of at least about 50, a roughness that corresponds to a Pp value of at least about 90, a roughness that corresponds to a Pt value of at least about 200, or a roughness that corresponds to a Pq value of at least about 60. In yet other embodiments, at least one surface of the metallic matrix that is surgically installed in accordance with the present methods has a roughness that corresponds to a Pa value of at least about 70, a roughness that corresponds to a Pp value of at least about 120, a roughness that corresponds to a Pt value of at least about 300, or a roughness that corresponds to a Pq value of at least about 70. The metallic matrix of the implant that is surgically installed pursuant to the present methods may comprise titanium, a titanium alloy, a cobalt-chromium alloy, molybdenum, tantalum, niobium, zirconium, stainless steel, or any combination thereof.

EXAMPLES

Example 1

Topography of Green Body Impacted with Particulate Material

Figure 2A:
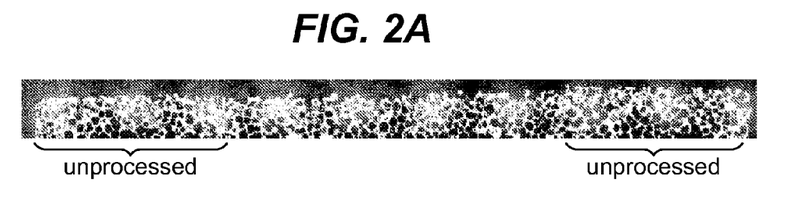
FIGS. 2A and 2B each show lateral surface profiles of green bodies of which the section in the middle has been processed in accordance with the inventive methods, while the sections near the ends were unprocessed.
Figure 2B:
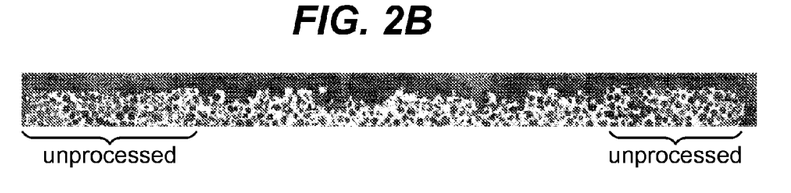

FIGS. 2A and 2B each depict a lateral view of a cross section through the surface of a green body of which certain sections have been impacted with a particulate material for a time and under conditions effective to displace a portion of the metal powder from the green body. For comparative purposes, sections near the ends of each green body (marked by brackets) were not processed in accordance with the present invention, i.e., were not impacted with the particulate material. The surface characteristics of the unprocessed sections are easily distinguishable from those of the sections of the green body that were impacted with the particulate material. In each image, the white material is the metal matrix, and black represents pores or empty space. The green body in FIG. 2A comprises compacted metal powder of Commercially Pure ("CP") Ti and was impacted with a particulate material comprising sodium chloride, ejected at a pressure of 15 psi from an orifice located about 6 inches from the green body for about 2 seconds. The green body in FIG. 2B comprises compacted metal powder of CP Ti and was impacted with a particulate material comprising sodium chloride, ejected at a force of 25 psi from an orifice located about 12 inches from the green body for 2 seconds. The conditions under which the green body in FIG. 2B was impacted with the particulate material resulted in more significant displacement of metal powder from the surface of the green body, thereby yielding larger and deeper pits, and by extension, higher peaks.

Example 2

Variation of Parameters of Impacting Process

Table 1, below, depicts three exemplary embodiments in which parameters of the impacting process were varied:

TABLE 1

| Type of Green Body | Particulate Material | Impacting Pressure (psi) | Working Distance (in) | Time (sec) | Green Body Translation (rpm) |
|---|---|---|---|---|---|
| Rabbit distal femur implant (cylindrical) | <250 μm NaCl (NaCl particles smaller than 250 μm in largest dimension) | 5 | 3 | 4 | 15 |
| 58 mm diameter acetabular cup | <250 μm NaCl | 20 | 7 | 10 | 50 |
| 1in² friction coupon (rectangular prism) | <250 μm NaCl | 20 | 12 | 3 | none |
| 1.25 inch diameter coupon | <250 μm NaCl | 10 | 2 | 2 | none |
| 1.25 inch diameter coupon | <250 μm NaCl | 10 | 4 | 2 | none |
| 1.25 inch diameter coupon | <250 μm NaCl | 15 | 2 | 2 | none |
| 1.25 inch diameter coupon | <250 μm NaCl | 15 | 4 | 2 | none |

Favorable results were obtained with respect to each of the green bodies that were subjected to an impacting process under the respective conditions described in Table 1; each of the green bodies featured roughened surfaces as compared with untreated green bodies.

Example 3

Measurement of Static Friction Coefficient

Figure 3:
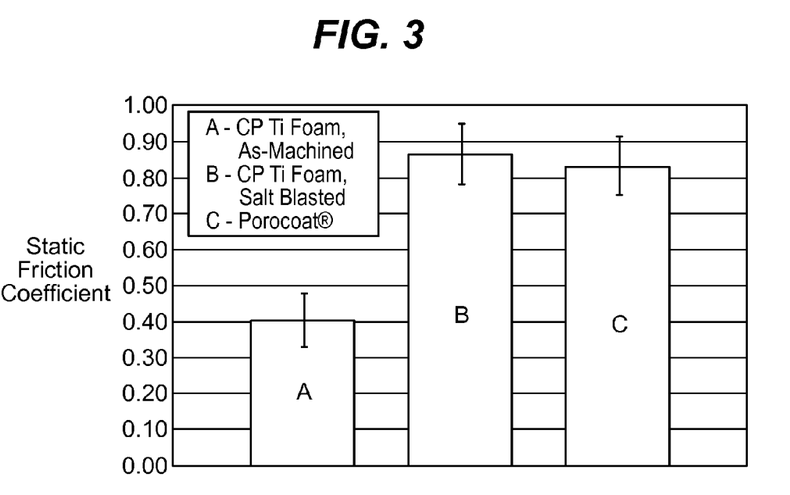
FIG. 3 provides measurements of static friction coefficient of various materials against a polymer bone analogue.
Figure 4:
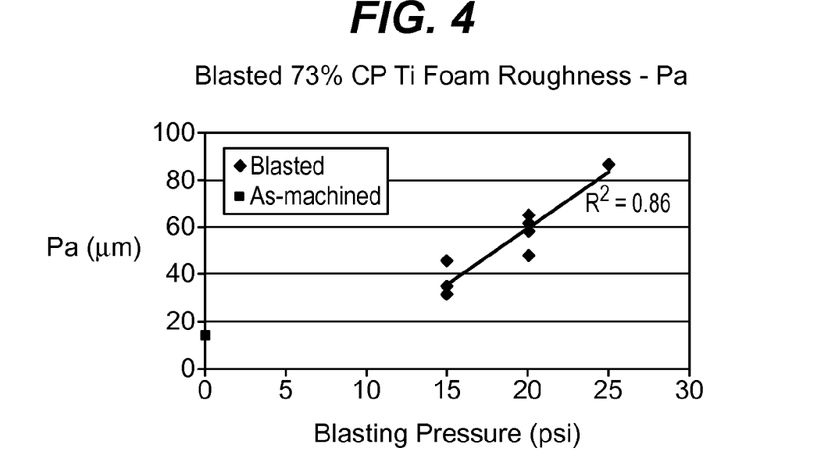
FIG. 4 depicts a graph that compares surface roughness of a CP-Ti metallic matrix sample with the pressure (psi) at which the green body sample from which the metallic matrix sample was prepared was impacted ("blasted") with the particulate material, wherein the surface roughness is expressed in terms of the Pa parameter.
Figure 5:
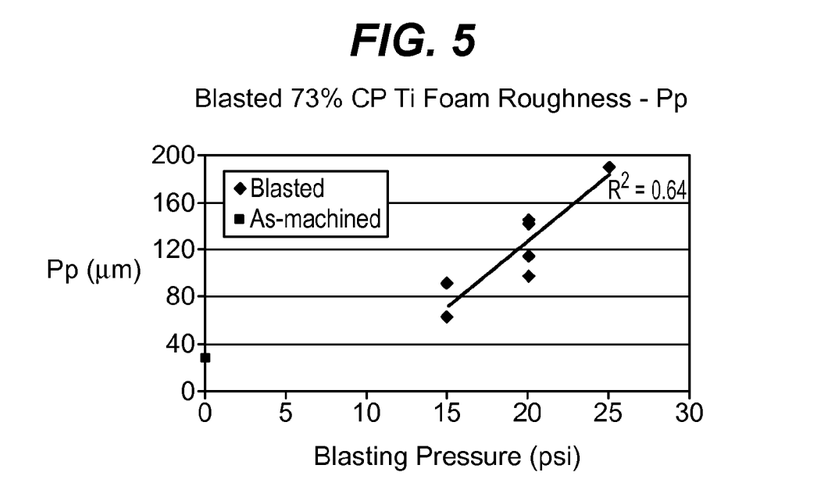
FIG. 5 depicts a graph that compares surface roughness of a CP-Ti metallic matrix sample with the pressure (psi) at which the green body sample from which the metallic matrix sample was prepared was impacted ("blasted") with the particulate material, wherein the surface roughness is expressed in terms of the Pp parameter.
Figure 6:
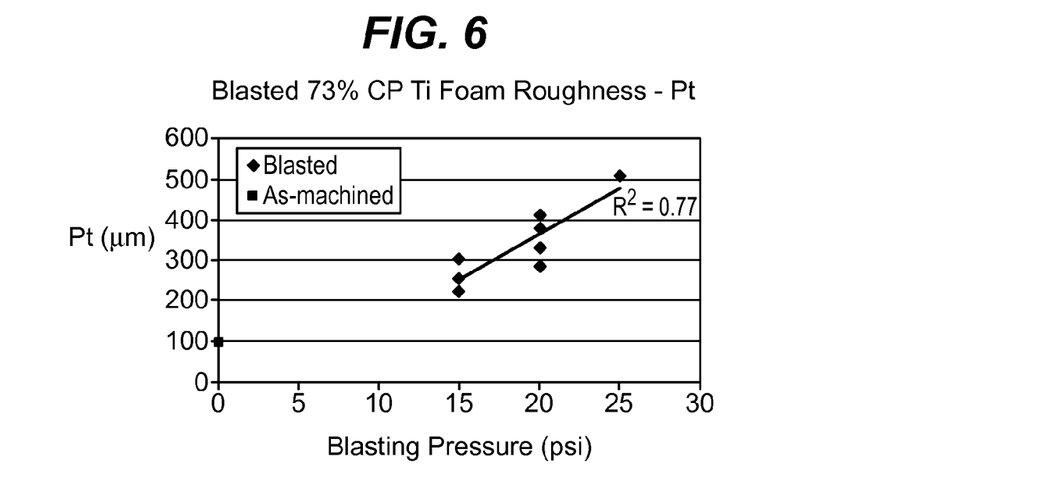
FIG. 6 depicts a graph that compares surface roughness of a CP-Ti metallic matrix sample with the pressure (psi) at which the green body sample from which the metallic matrix sample was prepared was impacted ("blasted") with the particulate material, wherein the surface roughness is expressed in terms of the Pt parameter.
Figure 7:
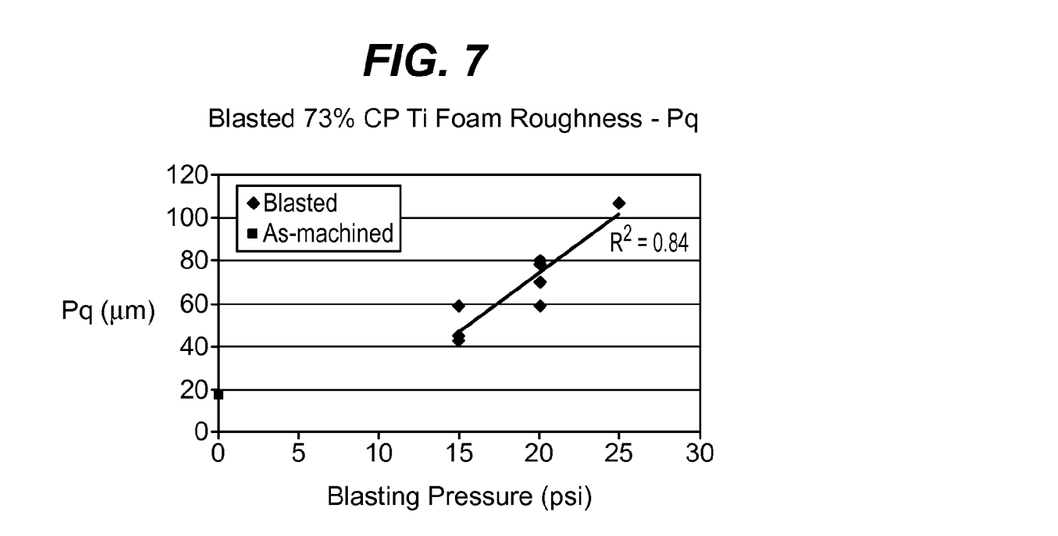
FIG. 7 depicts a graph that compares surface roughness of a CP-Ti metallic matrix sample with the pressure (psi) at which the green body sample from which the metallic matrix sample was prepared was impacted ("blasted") with the particulate material, wherein the surface roughness is expressed in terms of the Pq parameter.
Figure 8:
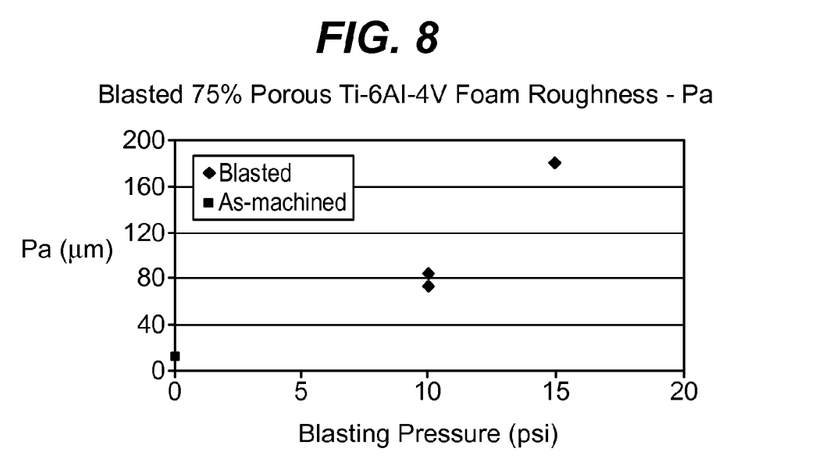
FIG. 8 depicts a graph that compares surface roughness of a Ti-6Al-4V metallic matrix sample with the pressure (psi) at which the green body sample from which the metallic matrix sample was prepared was impacted ("blasted") with the particulate material, wherein the surface roughness is expressed in terms of the Pa parameter.
Figure 9:
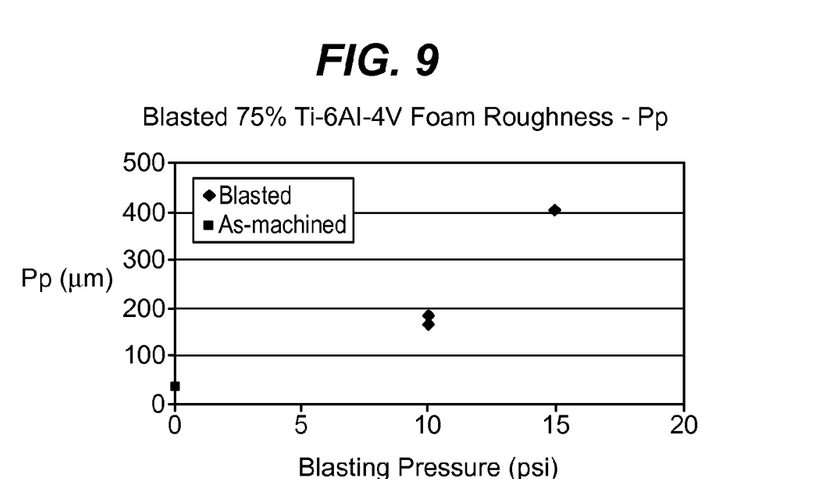
FIG. 9 depicts a graph that compares surface roughness of a Ti-6Al-4V metallic matrix sample with the pressure (psi) at which the green body sample from which the metallic matrix sample was prepared was impacted ("blasted") with the particulate material, wherein the surface roughness is expressed in terms of the Pp parameter.
Figure 10:
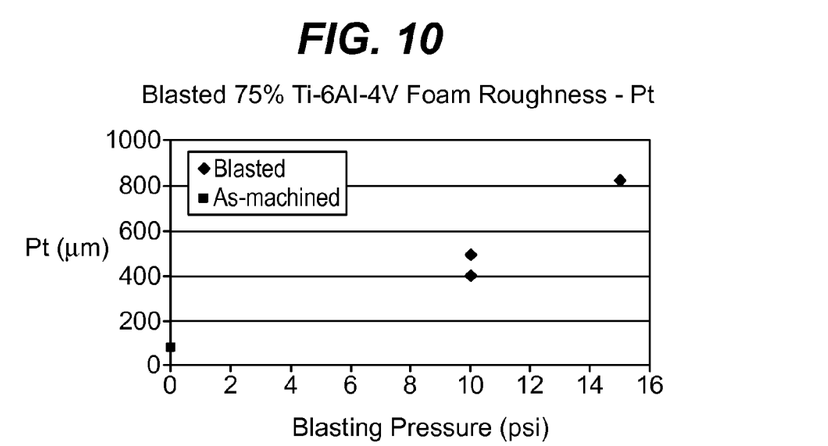
FIG. 10 depicts a graph that compares surface roughness of a Ti-6Al-4V metallic matrix sample with the pressure (psi) at which the green body sample from which the metallic matrix sample was prepared was impacted ("blasted") with the particulate material, wherein the surface roughness is expressed in terms of the Pt parameter.

Static friction coefficient was measured as between each of three different materials (each of materials A-C, as shown in FIG. 3) and a bone analogue, specifically Cat. No. FR-4520 from General Plastics Manufacturing Co. (Tacoma, Wash.), said to be a "rigid, closed-cell polyurethane foam" with a density of 20 lb/ft³. The first material (A) was a sintered, CP Ti foam structure of roughly 75% volume porosity that was prepared in accordance with the conventional "space holder" technique. The surface tested on this sample was machined flat while the sample was in the green state. The second material (B) was a sintered CP Ti foam structure of roughly 75% volume porosity. The surface tested on these samples was also machined flat while the sample was in the green state, but the surface was then also impacted with NaCl according to the conditions listed in Table 1; the test surface of the second material was therefore prepared in accordance with an embodiment of the present invention. The third material (C) consisted of POROCOAT® beaded porous coating (DePuy Orthopaedics, Inc., Warsaw, Ind.), a sintered coating of spherical unalloyed titanium beads on a Ti-6Al-4V susbtrate.

As shown in FIG. 3, material B had a static friction coefficient with the bone analogue that was comparable with that of material C, and statistically higher than the static friction coefficient measured with respect to material A, which is a metallic matrix that was prepared in accordance with the conventional "space holder" approach.

Example 4

Additional Measurements of Static Friction Coefficient Involving Exemplary Embodiments Static friction coefficient was measured for 0.75 in×0.75 square metallic matrix samples prepared from CP Ti or Ti-6Al-4V under 30 or 45 ksi cold isostatic compaction and otherwise in accordance with the conventional "space holder" technique, and having a porosity of about 73% or about 75% after sintering. The samples were either subjected to impaction by NaCl particles (Morton's Popcorn Salt®) of which at least 95% by weight were smaller than 250 μm, or were machined in the green state without being subjected to impaction with a particulate material. For the samples that were subjected to impaction, the particulate material comprising sodium chloride was ejected at a force of 5 psi, 10 psi, 15 psi, 20 psi, or 25 psi from an orifice located about 4 to 8 inches from the green body; two passes of the "blast" stream, with the blasting apparatus moving at about 1 inch/s, were performed with respect to each sample.

The friction test was performed using a "sled on a plane" method. The "sled" consisted of the 0.75 in×0.75 square metallic matrix samples, whereas each "plane" was a milled sample of Last-A-Foam® 6720 (General Plastics Manufacturing Company, Tacoma, Wash.), a rigid, closed-cell polyurethane foam with a density of 20 lb/ft³. Each sled was connected to a 250 N load cell by 10 lb monofilament line and pulled at 10 mm/min for 0.8 in. A weight was placed on the sled to create a normal force of 30 N. The static friction coefficient was calculated from the maximum force recorded before the first 0.5 N drop in force. Each sample was subjected to three separate test runs, and was ultrasonically cleaned in acetone between tests. The results are depicted in Tables 2 and 3, below:

TABLE 2

| Blasting Pressure (psi) | 74% Porosity/45 ksi compaction | | | | 73% Porosity/45 ksi compaction | | | | 73% Porosity/30 ksi | |
|---|---|---|---|---|---|---|---|---|---|---|
| | CP Ti | | Ti64 | | CP Ti | | Ti64 | | CP Ti | |
| | Avg | Std Dev | Avg | Std Dev | Avg | Std Dev | Avg | Std Dev | Avg | Std Dev |
| As-Machined | 0.52 | 0.1 | 0.65 | 0.01 | | | | | | |
| 5 | | | | | | | 0.83 | 0.06 | | |
| 10 | 0.72 | 0.14 | 1.09 | 0.21 | | | 0.97 | 0.11 | | |
| 15 | 0.89 | 0.18 | 1.35 | 0.09 | 0.69 | 0.06 | 1.02 | 0.07 | 0.87 | 0.07 |
| 20 | | | | | 0.87 | 0.09 | | | 0.96 | 0.07 |

TABLE 3

| Blasting Pressure (psi) | 75% Porosity/45 ksi compaction | | | | | | | |
|---|---|---|---|---|---|---|---|---|
| | CP Ti | | | | Ti64 | | | |
| | Avg | Std Dev | Max | Min | Avg | Std Dev | Max | Min |
| As-Machined | 0.52 | 0.1 | n = 1 | | 0.65 | 0.01 | n = 1 | |
| 5 | | | | | | | | |
| 10 | 0.72 | 0.14 | 0.74 | 0.67 | 1.09 | 0.21 | 1.30 | 0.99 |
| 15 | 0.89 | 0.18 | 0.98 | 0.82 | 1.35 | 0.17 | 1.51 | 1.10 |
| 20 | | | | | | | | |

Static friction coefficient ranged from about 0.7 to about 1.5, and included values of, inter alia, about 0.5, about 0.6, about 0.7, about 0.8, about 0.9, about 1.0, about 1.1, about 1.2, about 1.3, about 1.4, and about 1.5.

Example 5

Correlation Between Pressure Used During Impacting ("Blasting") Process and Surface Roughness FIGS. 4-10 depict graphs that compare average surface roughness values obtained from metallic matrix samples with the pressure (psi) at which the corresponding green body sample from which the metallic matrix samples were prepared was impacted ("blasted") with the particulate material. The graphs are labeled to indicate the material from which the metallic matrix was prepared (CP Ti or Ti-6Al-4V) and the porosity of the sample (73% or 75%). Surface roughness was assessed using a Zeiss Surfcomm 5000 (Carl Zeiss Inc., Germany) contact profilometer fitted with a 500 µm radius ruby ball as the stylus. Ten parallel 14-mm long traces were acquired from each sample, spaced about 1.5 mm apart to obtain measurements of the unfiltered P profile with a measurement speed of 0.3 mm/sec and a "least square straight" tilt correction, a. Pa (FIGS. 4 and 8) represents the arithmetic average value of the unfiltered raw profile departure from the mean line within a sampling length; Pp (FIGS. 5 and 9) is the largest peak deviation of the unfiltered raw roughness profile from the mean line within a sampling length; Pt (FIGS. 6 and 10) is the maximum peak to valley height of the unfiltered raw profile in the evaluation length; and Pq (FIG. 7) is the square root of the mean of all the 'z' values after they have been squared, defined over one sampling length. These parameters are pursuant to ISO 4287 (1997). In FIGS. 4-10, diamonds (♦) represent samples having surfaces that were subjected to impaction with particulate material while in the green state in accordance with the presently disclosed techniques, whereas the squares (■) represent samples that were machined in the green state and not subjected to the impacting procedure.

Table 4, below, provides the compiled average surface roughness measurements for CP-Ti metallic matrices having a porosity of about 73% that were prepared from green bodies that were impacted with a particulate material in accordance with the presently disclosed techniques. Surface roughness is expressed in terms of the Pa, Pp, Pt, and Pq parameters, respectively, as defined above.

TABLE 4

| | Blasting Pressure (ksi) | Pa | Pp | Pt | Pq |
|---|---|---|---|---|---|
| CP-Ti | 0 | 18.6 | 49.0 | 129.2 | 24.5 |
| | 10 | 52.9 | 126.5 | 360.6 | 66.9 |
| | 15 | 58.4 | 126.8 | 367.7 | 73.3 |
| | 20 | 58.1 | 124.3 | 351.2 | 71.9 |
| | 25 | 86.6 | 188.4 | 509.7 | 107.0 |

Table 5, below, provides the compiled average surface roughness measurements for Ti-64 metallic matrices having a porosity of about 75% that were prepared from green bodies that were impacted with a particulate material in accordance with the presently disclosed techniques, or sintered in the as-machined state (i.e., were not impacted with particulate material while in the green state). Surface roughness is expressed in terms of the Pa, Pp, Pt, and Pq parameters, respectively, as defined above.

TABLE 5

| | Blasting Pressure (ksi) | Pa | Pp | Pt | Pq |
|---|---|---|---|---|---|
| Ti-64 | 0 | 12.7 | 37.1 | 85.6 | 15.8 |
| | 10 | 78.6 | 178.8 | 444.2 | 96.6 |
| | 15 | 181.4 | 402.8 | 816.7 | 212.8 |
| | 20 | | | | |
| | 25 | | | | |

Table 6, below, provides the average surface roughness measurements for CP-Ti metallic matrices having a porosity of either about 73% or about 75% (as labeled) that were prepared from green bodies that were either impacted with a particulate material in accordance with the presently disclosed techniques, or sintered in the as-machined state (i.e., were not impacted with particulate material while in the green state). Surface roughness is expressed in terms of the Pa, Pp, Pt, and Pq parameters, respectively, as defined above.

TABLE 6

| | Sample Name | Blasting Pressure (ksi) | Pa | Pp | Pt | Pq |
|---|---|---|---|---|---|---|
| 73% porous CPTi | 15-4-1 | 15 | 34.5 | 63 | 226.9 | 44.9 |
| | 15-6-1 | 15 | 45.8 | 91.6 | 303.6 | 59.1 |
| | 15-8-1 | 15 | 31.3 | 61.6 | 257.3 | 42.2 |
| | 20-4-1 | 20 | 48.0 | 97.7 | 288.4 | 59.1 |
| | 20-6-1 | 20 | 61.7 | 144 | 408.6 | 78.3 |
| | 20-8-1 | 20 | 57.5 | 113 | 327.9 | 70.1 |
| | 20-6-2 | 20 | 65.3 | 141 | 379.9 | 80.2 |
| | 25-6-2 | 25 | 86.6 | 188 | 509.7 | 107.0 |
| | as-machined 73% | 0 | 13.8 | 37.8 | 94.1 | 17.3 |
| 75% porous CPTi | as-machined 0.75 | 0 | 18.6 | 49.0 | 129.2 | 24.5 |

Table 7, below, provides the average surface roughness measurements for Ti-6Al-4V metallic matrices having a porosity of either about 73% or about 75% (as labeled) that were prepared from green bodies that were either impacted with a particulate material in accordance with the presently disclosed techniques, or sintered in the as-machined state (i.e., were not impacted with particulate material while in the green state). Surface roughness is expressed in terms of the Pa, Pp, Pt, and Pq parameters, respectively, as defined above.

TABLE 7

| | Sample Name | Blasting Pressure (ksi) | Pa | Pp | Pt | Pq |
|---|---|---|---|---|---|---|
| 75% porous Ti—6Al—4V | b-3 | 10 | 83.2 | 186.8 | 491.1 | 103.0 |
| | a-3 | 10 | 74.0 | 170.7 | 397.2 | 90.2 |
| | c-4 | 15 | 181.4 | 402.8 | 816.7 | 212.8 |
| | As-machined 75% Ti—6Al—4V | 0 | 12.7 | 37.1 | 85.6 | 15.8 |

While the invention has been described and illustrated with reference to specific embodiments, those skilled in the art will recognize that modifications and variations may be made without departing from the principles of the invention as described herein and set forth in the following claims.

What is claimed:

1. An implant comprising a metallic matrix, made by a method comprising:
   mixing at least one metal powder with extractable particles of salt or sugar, thereby forming a powder mixture in which said metal powder and extractable particles assume respective positions;
   shaping said powder mixture into a shaped object;
   compacting said shaped object to form a green body;
   exposing said green body to a solvent in which said extractable particles are soluble to remove at least a portion of said extractable particles thereby forming a green body having a porosity of about 50 to 90%; and
   impacting said green body that has been exposed to said solvent with a particulate material for a time and under conditions effective to displace a portion of said metal powder from said green body, said particulate material being soluble in an aqueous fluid;
   immersing said green body that has been impacted with a particulate material in a bath comprising an aqueous fluid to remove said particulate material;
   sintering said green body having a portion of said metal powder displaced therefrom to form the implant;
   wherein at least one surface of the metallic matrix has a roughness that corresponds to a Pa value of at least 50, a roughness that corresponds to a Pp value of at least 90, a roughness that corresponds to a Pt value of at least 200, or a roughness that corresponds to a Pq value of at least 60.

2. The implant according to claim 1, wherein said powder mixture comprises about 18 wt. % to about 67 Wt. % metal powder, the balance of said powder mixture comprising said extractable particles.

3. The implant according to claim 1, wherein said extractable particles are soluble in an aqueous solvent, an organic solvent, or both.

4. The implant according to claim 3, wherein said green body is immersed in said solvent to remove said extractable particles.

5. The implant according to claim 1, wherein said extractable particles are sodium chloride, potassium chloride, sucrose, potassium sorbate, or any combination thereof.

6. The implant according to claim 5, wherein said metal powder comprises titanium, a titanium alloy, a cobalt-chromium alloy, molybdenum, tantalum, niobium zirconium, stainless steel, or any combination thereof.

7. The implant according to claim 1, wherein said particulate material comprises a salt.

8. The implant according to claim 1, wherein said particulate material comprises particles having an average diameter of about 150 μm to about 1250 μm.

9. The implant according to claim 1, wherein said particulate material impacts said green body with a pressure of about 3 psi to about 25 psi.

10. The implant according to claim 1, wherein impacting is effected for no more than about 2 seconds to about 30 seconds.

11. The implant according to claim 1, wherein said particulate material is ejected from an orifice that is positioned about 2 inches to about 30 inches from said green body.

12. The implant according to claim 1, wherein said metal powder comprises titanium or a titanium alloy; said extractable particles are sodium chloride or potassium chloride; said particulate material comprises a salt; and said green body is exposed to an aqueous solvent to remove said extractable particles.

13. The implant according to claim 1 where the impacting step is carried out using a blasting pressure ranging from 10 to 25 psi.

14. An implant made by a process comprising:
   mixing at least one metal powder comprising titanium or titanium alloy, with extractable particles of sodium chloride or potassium chloride, thereby forming a powder mixture in which said metal powder and extractable particles assume respective positions;
   shaping said powder mixture into a shaped object;
   compacting said shaped object to form a green body;
   exposing said green body to an aqueous solvent in which said extractable particles are soluble to remove at least a portion of said extractable particles thereby forming a green body having a porosity of about 50 to 90%; and
   impacting said green body that has been exposed to said solvent with a particulate material comprising a salt for a time and under conditions effective to displace a portion of said metal powder from said green body;
   immersing said green body that has been impacted with a particulate material in a bath comprising an aqueous fluid to remove said particulate material; and sintering said green body having a portion of said metal powder displaced therefrom to form an implant having a roughness that corresponds to a Pa value of at least 50.

* * * * *